US006384000B1

(12) United States Patent
McFann et al.

(10) Patent No.: US 6,384,000 B1
(45) Date of Patent: May 7, 2002

(54) PREDOMINANTLY SYNTHETIC BAR COMPRISING HYDROXY ACID SALT AND SPECIFIC TYPES AND AMOUNTS OF FILLER

(75) Inventors: Gregory Jay McFann, North Bergen; Charles Craig Nunn, Rutherford, both of NJ (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/837,009

(22) Filed: Apr. 18, 2001

(51) Int. Cl.[7] .................................................. A61K 7/50

(52) U.S. Cl. ....................... 510/152; 510/141; 510/155; 510/477

(58) Field of Search ................................. 510/152, 153, 510/155, 141, 477

(56) References Cited

U.S. PATENT DOCUMENTS

| | | | | |
|---|---|---|---|---|
| 4,046,717 A | | 9/1977 | Johnston et al. | |
| 4,268,424 A | | 5/1981 | Hall et al. | |
| 5,091,171 A | | 2/1992 | Yu et al. | |
| 5,393,466 A | | 2/1995 | Ilardi et al. | |
| 5,981,451 A | | 11/1999 | Farrell et al. | |
| 6,218,348 B1 | * | 4/2001 | Aronson et al. | 510/153 |
| 6,242,399 B1 | * | 6/2001 | Chambers et al. | 510/154 |

* cited by examiner

*Primary Examiner*—Necholus Ogden
(74) *Attorney, Agent, or Firm*—Ronald A. Koatz

(57) ABSTRACT

The invention discloses bars and process for making bars comprising synthetic anionic, fatty acid soap and hydroxy acid salt wherein bar can be extruded at minimum rates and wherein the bar and process are defined by specified ratio of hydroxy acid salt to calcite filler.

5 Claims, No Drawings

PREDOMINANTLY SYNTHETIC BAR COMPRISING HYDROXY ACID SALT AND SPECIFIC TYPES AND AMOUNTS OF FILLER

FIELD OF THE INVENTION

The invention relates to bars comprising synthetic anionic surfactant (e.g., directly esterified fatty acid isethionate or DEFI) and a lesser level of fatty acid soap (anionic/soap system). The invention further relates to process for incorporating alpha or beta hydroxy acid salt (e.g., alpha or beta hydroxy acid salt such as, for example (sodium lactate) while greatly enhancing processability relative to other bars in which the art has attempted to incorporate such hydroxy acid salts.

BACKGROUND

It has been difficult in the past to produce a manufacturable personal washing bar containing alpha or beta hydroxy acid salts (e.g., sodium lactate or potassium glycolate) because of the deleterious interactions between the salt and either soap or anionic surfactant. As a result, formulations containing, for example, alpha hydroxy acids (AHAS) or AHA salts are extremely soft, sticky and work sensitive. In the subject invention, it has been unexpectedly discovered that a far more processable anionic/soap formulation can be made by adjusting the ratio of hydroxy acid salt (which causes the formulation to be soft and sticky) to calcite filler (which causes the formulation to be hard and crumbly.)

Bars containing anionic surfactant, soap and hydroxy acid salts (e.g., AHA salts) are broadly known. U.S. Pat. No. 4,046,717 to Johnston et al, for example, discloses moisturizing detergent bar (including soap) containing lactate or mixtures of lactate and glutamate. In contrast to subject invention, there is no mention of filler (e.g., calcite filler) or of interaction between filler and alpha hydroxy acid (AHA) salt to improve processability.

Similarly, U.S. Pat. No. 4,268,424 to Hall discloses bar containing surfactant, soap and various moisturizers, but there is no mention of filler, in particular fillers such as calcite or of their interaction with hydroxy acid salts.

U.S. Pat. No. 5,981,451 to Farrell et al. describes a dry mix process (the present invention is generally practiced as melt process) for combining anionic (e.g., DEFI)/soap noodles) with soap and filler. Hydroxy acid salts are not mentioned anywhere.

Applicants have also filed several applications relating to modifying the material properties of formulations containing hydroxy acids or salts. In a co-pending application to Fair et al., filed same date as the subject application, applicants disclose incorporation of relatively high levels of hydroxy acids and/or salts into synthetic surfactant compositions. The compositions generally have pH of about 4–5, preferably close to 4 and, in contrast to compositions of the subject invention, cannot contain soap because of the acidic pH. Further, because of lower pH, these compositions would not tolerate calcite. Fair discloses that hydroxy acids or salts can be made more suitable for extrusion (e.g., less sticky) in formulations containing anionic and hydroxy acids or salts by adding polyol ester (e.g., glycerol monolaurate).

In a separate application, also filed on the same date as the subject application, applicants disclose use of monoglyceride (glycerol monolaurate) to help incorporate hydroxy acid into a soap bar. The application does not, however, disclose use of calcite fillers to enhance processing. Also, it is a soap bar.

In none of the art of which applicants are aware has anyone disclosed that processing can, in formulations comprising anionictsoapihydroxy acid salt (e.g., sodium lactate), be significantly improved by balancing ratio of calcite filler to alkali metal hydroxy acid salt (alpha or beta).

BRIEF DESCRIPTION OF THE INVENTION

The present invention relates to a bar composition and to process for significantly enhancing procesability of said bars which comprise hydroxy acid salt (e.g., as measured by extrusion rate and/or qualitative behavior, that is they tend to be less is sticky) by in turn balancing ratio of hydroxy acid salt to calcite filler.

More specifically, the invention comprises a bar comprising:

(a) 10% to 50%, preferably 15 to 45% by wt. anionic (e.g., directly esterified fatty acid isethionate);

(b) 5 to 30%, preferably 6 to 25% fatty acid soap (ratio of anionic to soap generally being greater than 1:1); and (c) 2 to 20%, preferably 3 to 15% hydroxy acid salt, wherein said bar can be extruded at rate of at least 150 grams/minute as measured in a laboratory scale extruder, wherein said bar comprises sufficient calcite filler (e.g., 1 to 30%, preferably 2 to 25%) such that ratio of calcite filler to hydroxy acid salt is above about 0.75, preferably 0.8:1 to 2:1, more preferably 0.9:1 to 2:1.

The balance will vary on a case to case basis depending on amount of anionic and/or soap and level of salt, but generally is in a range of about 1:1.

In a second embodiment, the invention relates to a process for making a more extrudable bar by adjusting ratio of calcite filler to hydroxy acid salt to be in the range of about 0.75:1 to 2:1.

DETAILED DESCRIPTION OF INVENTION

The invention relates to bar composition and process for ensuring delivery of greater amounts of hydroxy acid salt to an anionic/soap composition while retaining good processing/extrudability. The composition and process are dependent on balancing ratio of hydroxy acid salt to calcite filler. That is, addition of hydroxy acid salt may make bar too sticky to process. On the other hand, use of too much calcite filler may create a brittly, crumbly bar.

The composition comprises:

(a) 10 to 50% by wt. anionic surfactant (which can be combined with one or more other surfactants);

(b) 5 to 30% by wt. fatty acid soap (ratio of anionic to soap generally greater than 1:1);

(c) 2 to 20% by wt. hydroxy acid salt; and wherein said bar comprises sufficient calcite filler such that ratio of calcite filler to hydroxy acid salt is 0.75:1 to 2:1.

The bars can be extruded at rate of at least 150 grams/minute as measured in a laboratory scale extruder (e.g., 7.5 cm diameter, two-stage Weber Seelander Laboratory Plodder).

The various components (including optionals) are set forth below.

SURFACTANT SYSTEM

Bars made by the process of the subject invention comprise 10% to 50% by wt., preferably 15% to 45% anionic surfactant.

The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates.

Sulfosuccinates may be monoalkyl sulfosuccinates having the formula:

$$R^4O_2CCH_2CH(SO_3M)CO_2M; \text{ and}$$

amide-MEA sulfosuccinates of the formula;

$$R^4CONHCH_2CH_2O_2CCH_2CH(SO_3M)CO_2M$$

wherein $R^4$ ranges from $C_8$–$C_{22}$ alkyl and M is a solubilizing cation.

Sarcosinates are generally indicated by the formula:

$$R^1CON(CH_3)CH_2CO_2M,$$

wherein $R^1$ ranges from $C_8$–$C_{20}$ alkyl and M is a solubilizing cation.

Taurates are generally identified by formula:

$$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Particularly preferred are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 10% to about 70% by weight of the total bar composition. Preferably, this component is present from about 30% to about 60%.

The acyl isethionate may be an alkoxylated isethionate such as is described in ardi et al., U.S. Pat. No. 5,393,466, hereby incorporated by reference. This Compound has the general formula:

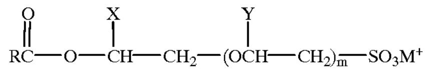

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In addition, the surfactant system may contain one or more optional surfactants selected from the group consisting of second synthetic anionic surfactant, amphoteric/zwitterionic surfactants, nonionic surfactants cationic surfactants and mixtures thereof. These may comprise 0 to 25%, preferably 1 to 15% by wt. of the composition.

The second anionic may be any of those discussed above.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

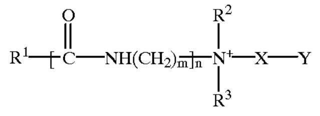

where $R^1$ is alkyl or alkenyl of 7 to 18 carbon atoms;

$R^2$ and $R^3$ are each independently alkyl, hydroxyalkyl or carboxyalkyl of 1 to 3 arbon atoms;

m is 2 to 4;

n is 0 to 1;

X is alkylene of 1 to 3 carbon atoms optionally substituted with hydroxyl, and

Y is $—CO_2—$ or $—SO_3—$

Suitable amphoteric detergents within the above general formula include simple betaines of formula:

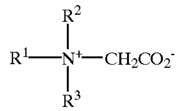

and amido betaines of formula:

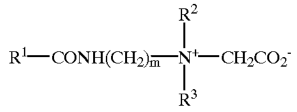

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

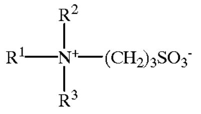

or

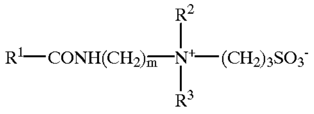

where m is 2 or 3, or variants of these in which $-(CH_2)_3SO_3-$ is replaced by

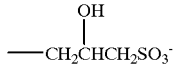

In these formulae $R^1$, $R^2$ and $R^3$ are as discussed previously.

The nonionic which may be used as the second component of the invention include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Examples of cationic detergents are the quatemary ammonium compounds such as alkyldimethylammonium halogenides.

Other surfactants which may be used are described in U.S. Pat. No. 3,723,325 to Parran Jr. and "Surface Active Agents and Detergents" (Vol. I & II) by Schwartz, Perry & Berch, both of which are also incorporated into the subject application by reference.

SOAP

The second required component of the invention is 5 to 30%, preferably 6 to 25% by wt. of a fatty acid soap. The amount of anionic should be in excess of amount of soap.

The term "soap" is used herein in its popular sense, i.e., the alkali metal or alkanol ammonium salts of aliphatic, alkane-, or alkene monocarboxylic acids. Sodium, potassium, magnesium, mono-, di- and tri-ethanol ammonium cations, or combinations thereof, are suitable for purposes of this invention. In general, sodium soaps are used in the compositions of this invention, but from about 1% to about 25% of the soap may be potassium or magnesium soaps. The soaps useful herein are the well known alkali metal salts of natural of synthetic aliphatic (alkanoic or alkenoic) acids having about 8 to 22 carbon atoms, preferably about 8 to about 18 carbon atoms. They may be described as alkali metal carboxylates of acrylic hydrocarbons having about 8 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight ranges.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85% fatty acids having about 12 to 18 carbon atoms.

Coconut oil employed for the soap may be substituted in whole or in part by other "high-alluric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil and ucuhuba butter.

A preferred soap is a mixture of about 30% to about 40% coconut oil and about 60% to about 70% tallow. Mixtures may also contain higher amounts of tallow, for example, 15% to 20% coconut and 80% to 85% tallow.

The soaps may contain unsaturation in accordance with commercially acceptable standards. Excessive unsaturation is normally avoided.

Soaps may be made by the classic kettle boiling process or modem continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

HYDROXY ACID SALT

Alpha-Hydroxy Acids

The generic structure of the alpha hydroxy acids of the invention is as follows:

$$(R_a)\ (R_b)C(OH)COOM$$

where $R_a$ and $R_b$ are H, F, Cl, Br; alkyl, aralkyl or aryl group of saturated or unsaturated, isomeric or non-isomeric, straight or branched chain or cyclic form, having 1 to 25 carbon atoms, and in addition $R_a$ and $R_b$ may carry OH, CHO, COOH and alkoxy group having 1 to 9 carbon atoms. The alpha hydroxy should be present in a salt form with an organic base or an inorganic alkali wherein salt may, for example, be sodium or potassium. The alpha hydroxy acid salts may exist as stereo isomers as D,L, and DL forms when $R_a$ and $R_b$ are not identical.

Typical alkyl, aralkyl and aryl groups for $R_a$ and $R_b$ include methyl, ethyl, propyl, isopropyl, butyl, pentyl, octyl, lauryl, stearyl, benzyl and phenyl, etc. The alpha hydroxy acids of the first group may be divided into (1) alkyl alpha hydroxy acids, (2) aralkyl and aryl alpha hydroxy acids, (3) polyhydroxy alpha hydroxy acids, and (4) polycarboxylic alpha hydroxy acids.

Typical alkyl alpha hydroxy acids from which the salt may be formed include 2-hydroxyethanoic acid (also known as glycolic acid or hydroxyacetic acid)

((H)(H)C(OH)COOH);

2-hydroxypropanoic acid (also known as lactic acid)

((($CH_2$)(H)C(OH)COOH);

2-methyl, 2 hydroxypropanoic acid (methyl lactic acid); 2-hydroxybutanoic acid, etc. Other examples are described at column 6 of U.S. Pat. No. 5,091,171 to Yu et al., hereby incorporated by reference into the subject application.

Examples of aralkyl and aryl alpha hydroxy acids from which salts may be formed include:

2-phenyl 2 hydroxyethanoic acid (mandellic acid)

(($C_6H_5$)(H)C(OH)(COOH);

2,2-diphenyl 2 hydroxyethanoic acid (benzilic acid)

(($CSH_5$)($C_6H_5$)C(OH)COOH);

Other examples are described at columns 6–7 of U.S. Pat. No. 5,091,171 to Yu et al.

Other acids from which salts may be formed are polyhydroxy alpha hydroxy acids such as 2,3-Dihydroxypropanoic acid (glyceric acid)

(($HOCH_2$)(H)C(OH)COOH);

and polycarboxylic alpha hydroxy acids such as 2-hydroxypropane-1,3-dioic acid (tartronic acid)

(HOOC(H)C(OH)COOH).

Again, other examples of these are shown in U.S. Pat. No. 5,091,171 to Yu et al.

Examples of β-hydroxy acid salts include sodium or potassium salicylate.

According to the subject invention, it is possible to incorporate up to levels of 20%, more preferably at least 3% to 15%, of these hydroxy acid salts. It has previously been extremely difficult or impossible to incorporate such high amounts of hydroxy acid salts into bars because, without wishing to be bound by theory, it is believed the hydroxy acid salts react with anionics to create a high liquid to solid ratio. This in turn may cause stickiness in, for example, the production of an extrusion bar or cause phase separation in cast melt bars. In the absence of a suitable structurant, it has simply not been feasible to incorporate such high levels of hydroxy acid into bars.

FILLER

The bar phase further comprises 1 to 30% by wt., preferably 2% to 25% by wt., inert filler, specifically, calcite filler (e.g., $CaCO_3$).

Unexpectedly, it has been found that calcite can be used with hydroxy acid salts when used in specific ratio of filler to hydroxy acid salt (e.g., 0.75:1 to 2:1) to form bars which have enhanced processing as measured by extrudability and qualitative behavior.

Optional Ingredients

Benefit Agents

The benefit agent can be an "emollient oil" by which is meant a substance which softens the skin (stratum corneum) by increasing into water content and keeping it soft by retarding decrease of water content.

Preferred emollients include:

(a) silicone oils, gums and modifications thereof such as linear and cyclic polydimethylsiloxanes; amino, alkyl alkylaryl and aryl silicone oils;

(b) fats and oils including natural fats and oils such as jojoba, soybean, rice bran, avocado, almond, olive, sesame, sunflower oil, persic, castor, coconut, mink oils; cacao fat; beef tallow, lard; hardened oils obtained by hydrogenating the aforementioned oils; and synthetic mono, di and triglycerides such as myristic acid glyceride and 2ethylhexanoic acid glyceride;

(c) waxes such as carnauba, spermaceti, beeswax, lanolin and derivatives thereof;

(d) hydrophobic plant extracts;

(e) hydrocarbons such as liquid paraffins, vaseline, microcrystalline wax, ceresin, squalene, pristan and mineral oil;

(f) higher fatty acids such as lauric, myristic, palmitic, stearic, behenic, oleic, linoleic, linolenic, lanolic, isostearic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins such as vitamin A and E, and vitamin alkyl esters, including those vitamin C alkyl esters;

(l) sunscreens such as octyl methoxyl cinnamate (Parsol MCX) and butyl methoxy benzoylmethane (Parsol 1789);

(m) phospholipids; and (n) mixtures of any of the foregoing components.

Other Optionals

In particularly preferred embodiments, it is desirable to use sunscreens, for example, Parsol MCX®, Eusolex® and Octocrylene.

In addition, the compositions of the invention may include optional ingredients as follows:

Organic solvents, such as ethanol; auxiliary thickeners, such as carboxymethylcellulose, magnesium aluminum silicate, hydroxyethylcellulose, methylcellulose, carbopols, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4'-trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24, Merquat®-polymer, and Jaguar® type conditioners from Rhone-Poulenc; and Salcare®-type conditioners from Allied Colloids.

Polyethylene glycols which may be used include:

| | | |
|---|---|---|
| Polyox | WSR-205 | PEG 14M, |
| Polyox | WSR-N-60K | PEG 45M, or |
| Polyox | WSR-N-750 | PEG 7M. |

PEG with molecular weight ranging from 300 to 10,000 Dalton, such as those marketed under the tradename of CARBOWAX SENTRY® by Union Carbide.

Another ingredient which may be included are exfoliants such as polyoxyethylene beads, walnut shells and apricot seeds The structurant of the invention can be a water soluble or water insoluble structurant.

Water soluble structurants include moderately high molecular weight polyalkylene oxides of appropriate melting point (e.g., 40° to 100° C., preferably 50° to 90° C.) and in particular polyethylene glycols or mixtures thereof.

Polyethylene glycols (PEG's) which are used may have a molecular weight in the range 2,000 to 25,000, preferably 3,000 to 10,000. However, in some embodiments of this invention it is preferred to include a fairly small quantity of polyethylene glycol with a molecular weight in the range from 50,000 to 500,000, especially molecular weights of around 100,000. Such polyethylene glycols have been found to improve the wear rate of the bars. It is believed that this is because their long polymer chains remain entangled even when the bar composition is wetted during use.

If such high molecular weight polyethylene glycols (or any other water soluble high molecular weight polyalkylene oxides) are used, the quantity is preferably from 1% to 5%, more preferably from 1 % to 1.5% to 4% or 4.5% by weight of the composition. These materials will generally be used jointly with a large quantity of other water soluble structurant such as the above mentioned polyethylene glycol of molecular weight 2,000 to 25,000, preferably 3,000 to 10,000.

Water insoluble structurants also have a melting point in the range 40–100° C., more preferably at least 50° C., notably 50° C. to 90° C. Suitable materials which are particularly envisaged are fatty acids, particularly those having a carbon chain of 12 to 24 carbon atoms. Examples are lauric, myristic, palmitic, stark, arachidic and behenic acids and mixtures thereof. Sources of these fatty acids are coconut, topped coconut, palm, palm kernel, babassu and tallow fatty acids and partially or fully hardened fatty acids or distilled fatty acids. Other suitable water insoluble structurants include alkanols of 8 to 20 carbon atoms, particularly cetyl alcohol. These materials generally have a water solubility of less than 5 g/litre at 20° C. Other structurants may include particulate solids such as talc, starch (e.g., maltodextrin) or clay.

The relative proportions of the water soluble structurants and water insoluble structurants govern the rate at which the bar wears during use. The presence of the water-insoluble structurant tends to delay dissolution of the bar when exposed to water during use and hence retard the rate of wear.

Water

Finally, bar compositions of the invention comprise about 1 to 15%, preferably 2 to 12%, more preferably 3 to 12% by wt. water.

Bar compositions of the invention have pH of about 6 to 8, preferably about 7 and above.

PROCESSING

According to the process which may be used to form compositions of the invention, a mixer is preheated to about 71° C. and free fatty acid (palmiticistearic acid) is put in and allowed to melt. If the formulation includes sodium stearate, NaOH is added at this point to generate the "stearate" (actually palmitate/stearate) in situ from part of the palmiticstearic acid. The mixer temperature is increased to about 82° C. in order to make sure that the stearate is solubilized in the fatty acid. Amphoteric surfactant (e.g., betaine) and hydroxy acid salt (e.g., sodium lactate) are then added. The mixer temperature drops rapidly, and the betaine, stearate, palmitic/stearic acid, and lactate form a single gelatinous mass. As the mixer temperature begins to climb again, DEFI, soap, filler, and minor ingredients are gradually added over a 1 hour period, and the batch is allowed to mix at a temperature of about 88° C. When all the ingredients are thoroughly mixed, the batch is dried down under vacuum to the target moisture level and dropped from the mixer. Sunflower oil may be added just before the batch is dropped in order to minimize the possibility of discoloration.

After the batch is dropped, it is passed over a chill roll set at 14° C., and collected into a sack, hopefully in the form of brittle chips, although formulations containing sodium lactate often take the form of large rubbery sheets coming off the chill roll. The rubbery sheets usually become brittle after 2–3 days storage. At that point, the chips are perfumed, passed through a 3.5 cm diameter plodder (e.g., Water Seelander plodder), and stamped into bars.

It should be noted that the process described above is a general hot mix process. Formulation properties are not dependent on specific process conditions (order of addition, mixing times, temperatures) and the invention is not intended to be, nor should be construed to have, any such limitation Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight. It should be noted that, when supplied as aqueous solution (e.g., sodium lactate, sodium isethionate, betaine), the percentages are based on 100% active ingredient.

EXAMPLES

In order to show the advantage of using specified ratio range of hydroxy acid salt to filler, applicants prepared the following examples.

| Ingredients | Base | Composition A | Composition B | Example 1 | Example 2 | Example 3 | Example 4 |
|---|---|---|---|---|---|---|---|
| Na cocoyl isethionate | 44.3 | 40.7 | 38.2 | 38.1 | 38.2 | 38.2 | 38.1 |
| Anhydrous soap | 21.7 | 20.0 | 11.8 | 11.8 | 11.8 | 13.8 | 11.7 |
| Palmitic-stearic acid | 14.0 | 12.9 | 15.0 | 19.1 | 17.1 | 17.1 | 17.1 |
| Sodium stearate | 4.6 | 4.2 | 4.0 | 4.0 | 40 | — | 2.0 |
| Sodium isethionate | 4.2 | 3.9 | 3.6 | 3.6 | 36 | 3.6 | 3.6 |
| Sodium chloride | 1.3 | 1.2 | 1.1 | 1.1 | 1.1 | 1.1 | 1.1 |
| Cocoamidopropyl betaine | 2.1 | 1.9 | 1.8 | 1.8 | 1.8 | 1.8 | 1.8 |
| $TiO_2$ | 0.4 | 0.4 | 0.3 | 0.3 | 0.3 | 0.3 | 0.3 |
| EHDP | 0.02 | 0.02 | 0.02 | 0.02 | 0.02 | 0.02 | 0.02 |
| EDTA | 0.02 | 0.02 | 0.02 | 0.02 | 0.02 | 0.02 | 0.02 |
| Water | 7.3 | 6.7 | 5.0 | 5.0 | 5.0 | 5.0 | 5.0 |
| Calcite | — | — | 1.11 | 7.0 | 7.0 | 9.0 | 9.0 |
| Sodium lactate | — | 8.0 | 8.1 | 8.1 | 8.1 | 8.1 | 8.1 |
| Sunflower seed oil | — | — | — | — | 2.0 | 2.0 | 2.0 |

A formulation without filler or lactate (base) was very hard and easy to plod. However, when 8% sodium lactate was added (Comparative A), it became soft, sticky, and virtually unprocessible, presumably because of the hydrotroping effect of the alpha hydroxy acid salt acting to increase the percent of liquid component. Adding 12% calcite had the opposite effect (Comparative B). This formulation was extremely crumbly and could not be formed into a cohesive billet.

It was hypothesized that a processable formulation might be achieved by balancing the sodium lactate and calcite loadings. This balance was achieved in formulation Example 1, which contained 7% calcite and 8% sodium lactate and had outstanding processibility, both on the chill roll and through the plodder.

Example 2 represented a modified form of Example 1 wherein an optional skin benefit agent (e.g., sunflower seed oil) was added to provide additional consumer benefit. The sunflower seed oil softened the bar slightly and decreased lather volume. Also, plodding on the laboratory plodder was slightly poorer (e.g., bar was slightly softer).

Example 1 formulation also had some drawbacks: it was draggy and tended to be gritty. The grit was traced to the sodium stearate component by the simple expedient of taking the stearate out (Example 3). Although grittiness was reduced, Example 3 was softer and stickier and more difficult to process. Example 4 was derived from Example 1, but contained 2% stearate instead of 4%. Its processibility was better than Example 3, but less than Example 1.

Notwithstanding these variations, all bars of the invention (with both hydroxy acid and filler) were processable and were clearly neither too liquidy nor too crumbly.

The Example clearly shows that some filler is needed to process bars containing hydroxy acid salt, but that the ratio of hydroxy acid salt to filler must be at certain level to ensure the bar is not too crumbly. That is the bars of the invention have the "plasticity" required for extrusion. They are neither too soft and sticky, nor too hard, brittie and crumbly.

What is claimed is:

1. A bar composition comprising:

(a) 10 to 50% by wt. anionic;

(b) 5 to 30% by wt. fatty acid soap;

(c) 2 to 20% hydroxy acid salt;

wherein bar is extruded at rate of at least 150 grams/minute in a laboratory scale extruder;

wherein the bar comprises sufficient calcite filler such that ratio of calcite filler to hydroxy acid salt is above about 0.75:1 to about 2:1; and wherein ratio of anionic to soap is greater than 1:1.

2. A bar according to claim 1, comprising 15 to 45% anionic.

3. A bar according to claim 1, comprising 6 to 25% fatty acid soap.

4. A bar according to claim 1, wherein hydroxy acid salt is alpha or beta hydroxy acid salt.

5. A bar according to claim 1, wherein the ratio of calcite filler to hydroxy acid salt is about 0.80:1 to about 2:1.

* * * * *